US009011827B2

(12) United States Patent
Bui et al.

(10) Patent No.: US 9,011,827 B2
(45) Date of Patent: Apr. 21, 2015

(54) COMPOSITION AND PROCESS FOR TREATING KERATINOUS SUBSTRATES WITH AT LEAST TWO IMMISCIBLE COSMETIC COMPOSITIONS

(75) Inventors: Hy Si Bui, Piscataway, NJ (US); Michell Chen, Edison, NJ (US); Padraig McDermott, Meudon (FR); Shao Xiang Lu, Plainsboro, NJ (US); Ashini Amin, Monroe, NJ (US); Mohamed Kanji, Edison, NJ (US); Dhaval Patel, Edison, NJ (US)

(73) Assignee: L'Oréal (FR)

( * ) Notice: Subject to any disclaimer, the term of this patent is extended or adjusted under 35 U.S.C. 154(b) by 1388 days.

(21) Appl. No.: 11/992,620

(22) PCT Filed: Sep. 22, 2006

(86) PCT No.: PCT/US2006/037333
§ 371 (c)(1),
(2), (4) Date: Apr. 10, 2009

(87) PCT Pub. No.: WO2007/038454
PCT Pub. Date: Apr. 5, 2007

(65) Prior Publication Data
US 2009/0246159 A1     Oct. 1, 2009

Related U.S. Application Data

(60) Provisional application No. 60/720,420, filed on Sep. 26, 2005.

(51) Int. Cl.
*A61K 8/891* (2006.01)
*A61Q 1/04* (2006.01)
*A61K 8/58* (2006.01)
*A61K 8/81* (2006.01)
*A61Q 1/02* (2006.01)

(52) U.S. Cl.
CPC . *A61Q 1/04* (2013.01); *A61K 8/585* (2013.01); *A61K 8/8111* (2013.01); *A61K 8/891* (2013.01); *A61Q 1/02* (2013.01); *A61K 2800/882* (2013.01); *A61K 2800/884* (2013.01)

(58) Field of Classification Search
None
See application file for complete search history.

(56) References Cited

U.S. PATENT DOCUMENTS

| | | | | |
|---|---|---|---|---|
| 5,665,368 A | * | 9/1997 | Lentini et al. | 424/401 |
| 6,403,107 B1 | * | 6/2002 | Lemann | 424/401 |
| 2002/0064539 A1 | * | 5/2002 | Philippe et al. | 424/401 |
| 2003/0108578 A1 | * | 6/2003 | Maubru | 424/401 |
| 2004/0086473 A1 | * | 5/2004 | Rabe et al. | 424/63 |
| 2004/0120911 A1 | * | 6/2004 | Shah et al. | 424/70.11 |
| 2004/0151680 A1 | * | 8/2004 | Patil et al. | 424/70.12 |
| 2004/0192832 A1 | * | 9/2004 | Cordier | 524/588 |
| 2004/0246156 A1 | * | 12/2004 | Schrodinger | 341/154 |
| 2005/0043475 A1 | * | 2/2005 | Blin | 524/588 |

FOREIGN PATENT DOCUMENTS

| | | | | |
|---|---|---|---|---|
| EP | 1 005 849 A1 | 6/2000 | | |
| EP | 1 064 926 A1 | 1/2001 | | |
| EP | 1 424 065 A1 | 6/2004 | | |
| GB | 2259015 | * | 8/1992 | A61K 7/48 |
| GB | 2 259 015 A | 3/1993 | | |
| JP | 03-034616 A | 2/2003 | | |
| JP | 2007-023036 A | 2/2007 | | |
| JP | 2008-542424 A | 11/2008 | | |
| WO | WO-02/069917 A2 | 9/2002 | | |
| WO | 03/105787 A2 | 12/2003 | | |
| WO | 03/105790 A1 | 12/2003 | | |
| WO | 2004/103302 A2 | 12/2004 | | |
| WO | 2006/026228 A1 | 3/2006 | | |

OTHER PUBLICATIONS

Dow Corning PH-1555 Product Information, 2004, pp. 1-4.*

* cited by examiner

*Primary Examiner* — Brian Gulledge
(74) *Attorney, Agent, or Firm* — Lerner, David, Littenberg, Krumholz & Mentlik, LLP

(57) ABSTRACT

A process for treating a keratinous substrate involving: (a) providing at least a first composition having a continuous phase whose major ingredient has a solubility parameter corresponding to δ; (b) providing at least a second composition having a continuous phase whose major ingredient has a solubility parameter corresponding to δ'; and (c) combining (a) and (b) prior to, or during, their application onto the keratinous substrate, and wherein the difference between δ and δ' is greater than 12, and wherein the major ingredient is chosen from a hydrophilic polar material, an organic non-polar material and an inorganic non-polar material.

31 Claims, No Drawings

COMPOSITION AND PROCESS FOR TREATING KERATINOUS SUBSTRATES WITH AT LEAST TWO IMMISCIBLE COSMETIC COMPOSITIONS

CROSS REFERENCE TO RELATED APPLICATIONS

The present application is a national phase entry under 35 U.S.C. §371 of International Application No. PCT/US2006/037333, filed Sep. 22, 2006, published in English, which claims benefit of United States Provisional Patent Application No. 60/720,420, filed Sep. 26, 2005. The disclosures of all of said applications are incorporated by reference herein.

BACKGROUND OF THE INVENTION

It is well known in the beauty care field that cosmetic compositions such as mascaras, lipsticks and foundations provide aesthetic benefits when applied onto the appropriate keratinous surface. For example, volumization is a desirable aesthetic benefit for eyelashes and lips in order to make them appear fuller, whereas transfer resistance, long wear and/or comfort are important features for lipsticks and foundations. Unfortunately, these aesthetic benefits are not always simultaneously achieved through the use of a single cosmetic product due to the challenge of formulating a homogeneous composition which satisfies these types of multiple consumer needs. For instance, a lipstick product with transfer resistance properties typically does not have good shine attributes, and vice-versa.

Thus, a need still exists for a cosmetic system capable of simultaneously imparting multiple aesthetic benefits via a single application step system.

SUMMARY OF THE INVENTION

The present invention relates to a process for treating a keratinous substrate involving the steps of:

(a) providing at least a first composition having a continuous phase whose major ingredient has a solubility parameter corresponding to $\delta$;

(b) providing at least a second composition having a continuous phase whose major ingredient has a solubility parameter corresponding to $\delta'$; and (c) combining (a) and (b) prior to, or during, their application onto the keratinous substrate, and wherein the difference between $\delta$ and $\delta'$ is greater than 12, greater than 11, greater than 10, greater than 9, greater than 8, greater than 7, greater than 6, greater than 5, greater than 4, greater than 3, greater than 2, greater than 1, greater than 0.5, greater than 0, and wherein the major ingredient is chosen from a hydrophilic polar material, an organic non-polar material and an inorganic non-polar material.

The present invention is also directed to a cosmetic system capable of imparting multiple aesthetic benefits onto a keratinous substrate in a single application comprising a multi-unit receptacle containing:

(a) at least a first unit comprising a composition having a continuous phase whose major ingredient has a solubility parameter corresponding to $\delta$; and (b) at least a second unit comprising a composition having a continuous phase whose major ingredient has a solubility parameter corresponding to $\delta'$, and wherein the difference between $\delta$ and $\delta'$ is greater than 12, greater than 11, greater than 10, greater than 9, greater than 8, greater than 7, greater than 6, greater than 5, greater than 4, greater than 3, greater than 2, greater than 1, greater than 0.5, greater than 0, and wherein the major ingredient is chosen from a hydrophilic polar material, an organic non-polar material and an inorganic non-polar material.

DETAILED DESCRIPTION other than in the operating examples, or where otherwise indicated, all numbers expressing quantities of ingredients and/or reaction conditions are to be understood as being modified in all instances by the term "about".

The present invention relates to a cosmetic system and process suitable for treating a keratinous substrate using a single application-step product. Surprisingly, the inventors of the present invention have found that it is possible to create a cosmetic system capable of imparting multiple aesthetic benefits in a single application step. The essential components of the cosmetic system are described below. Also included is a nonexclusive description of various optional and preferred components useful in embodiments of the present invention.

As used herein, "safe and effective amount" means an amount of a compound, component, or composition (as applicable) sufficient to significantly induce a positive effect (e.g., confer a noticeable cosmetic benefit), but low enough to avoid serious side effects, (e.g., undue toxicity or allergic reaction), i.e., to provide a reasonable benefit to risk ratio, within the scope of sound medical judgment.

As used herein, "cosmetic system" means any color cosmetic or skin care product. "Cosmetic systems" include, but are not limited to, products that leave color on the face, including make-up, liquid foundation, mascara, concealers, eye liners, brow colors, eye shadows, blushers, lip sticks, lip balms, face powders, solid emulsion foundations, powder foundations, and the like. The term "foundation" refers to liquid, cream, mousse, pancake, compact, concealer or like product created or reintroduced by cosmetic companies to even out the overall coloring of the skin. Additionally, "cosmetic systems" may include moisturizers, sunscreen products, self-tanning products, antiperspirant compositions, shaving creams, and skin cleansers.

The term "continuous phase" can have either its ordinary meaning in the art, as in the case of a composition which is a dispersion/suspension, or an aqueous emulsion, or a non-aqueous emulsion, or can refer to the sole phase, as in the case of a composition having a single phase.

The term "major ingredient" refers to the hydrophilic polar liquid, organic oil or inorganic oil present in the highest concentration.

Herein, "comprising" means that other steps and other ingredients which do not affect the end result can be added. This term encompasses the terms "consisting of" and "consisting essentially of". The products, compositions, and methods/processes of the present invention can comprise, consist of, and consist essentially of the essential elements and limitations of the invention described herein, as well as any of the additional or optional ingredients, components, steps, or limitations described herein.

All percentages, parts, and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

All measurements made are at 25° C., unless otherwise designated.

The present invention involves the use of at least two compositions, each of which having a continuous phase whose major ingredient is substantially incompatible with its counterpart such that when the at least two compositions are combined, their respective continuous phases are substantially incompatible with one another.

In order to determine whether the continuous phase of one composition is substantially incompatible with the continuous phase of another composition, the solubility parameter of each major ingredient present in its respective continuous phase must first be determined. Once the solubility parameter of each major ingredient is identified, the difference between the solubility parameters of the major ingredients is then calculated in order to determine whether the continuous phases are substantially incompatible.

According to the present invention, continuous phases are deemed to be substantially incompatible if the difference between the solubility parameters of the major ingredients present in their respective continuous phases is greater than 12, preferably greater than 11, more preferably greater than 10, more preferably greater than 9, more preferably greater than 8, more preferably greater than 7, more preferably greater than 6, more preferably greater than 5, more preferably greater than 4, more preferably greater than 3, more preferably greater than 2, more preferably greater than 1, more preferably greater than 0.5, and most preferably greater than 0. solubility parameters $\delta$ and $\delta'$ are determined according to the Hansen solubility space as defined in the article "Solubility Parameter Values" by Eric A. Grulke in the work "Polymer Handbook," 3rd edition, Chapter VII, pages 519-559, the entire content of which is hereby incorporated by reference, by the relationship:

$$\delta \text{ (or } \delta') = (d_D^2 + d_P^2 + d_H^2)^{1/2}, \text{ in which:}$$

$d_D$ characterizes the London dispersion forces resulting from the formation of dipoles induced during molecular impacts, $d_P$ characterizes the forces of Debye interactions between permanent dipoles, $d_H$ characterizes the forces of specific interactions (hydrogen bond, acid/base or donor/acceptor type and the like). The definition of the solvents in the three-dimensional solubility space according to Hansen is given in the article by C. M. Hansen: "The three-dimensional solubility parameters," J. Paint Technol., 39, 105 (1967), the entire content of which is hereby incorporated by reference.

1. Hydrophilic Polar-Materials

Examples of hydrophilic polar materials include, but are not limited to, water, alcohols, polyols, and the like.

More specific examples of hydrophilic polar materials useful herein include, but are not limited to, materials such as urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene; glycol, hexylene glycol, and the like; polyethylene glycol; sugars and starches; sugar and starch derivatives (e.g., alkoxylated glucose); hyaluronic acid; chitin, starch-grafted sodium polyacrylates such as Sanwet® IM-1000, IM-1500, and IM-2500: (available from Celanese Superabsorbent Materials); lactamide monoethanolamine; acetamide monoethanolamine; propoxylated glycerol (as described in U.S. Pat. No. 4,976,953); and mixtures thereof.

2. Organic Non-Polar Materials:

Nonlimiting examples of suitable organic non-polar materials include, but are not limited to:

(1) Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p. 415-417 (1993)

(2) Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, Drug. Cosmet. Ind., 89, 36-37, 76, 78-80, 82 (1961); and International Cosmetic Ingredient Dictionary, Fifth Edition, vol. 1, p. 537 (1993).

(3) Straight and branched chain hydrocarbons having from about 7 to about 40 carbon atoms. Nonlimiting examples of these hydrocarbon materials include dodecane, isododecane, squalane, cholesterol, hydrogenated polyisobutylene, polybutene, polydecene, docosane (i.e. a $C_{22}$ hydrocarbon), hexadecane, isohexadecane (a commercially available hydrocarbon sold as Permethyl® 101A by Presperse). Also useful are the $C_7$-$C_{40}$ isoparaffins, which are $C_7$-$C_{40}$ branched hydrocarbons.

(4) $C_1$-$C_{30}$ alcohol esters of $C_3$-$C_{30}$ carboxylic acids and of $C_2$-$C_{30}$ dicarboxylic acids, including straight and branched chain materials as well as aromatic derivatives (as used herein in reference to the hydrophobic component, mono- and polycarboxylic acids include straight chain, branched chain and aryl carboxylic acids). Nonlimiting examples include diisopropyl sebacate, diisopropyl adipate., isopropyl myristate, isopropyl palmitate, methyl palmitate, myristyl propionate, 2-ethylhexyl palmitate, isodecyl neopentanoate, di-2-ethylhexyl maleate, cetyl palmitate, myristyl myristate, stearyl stearate, isopropyl stearate, methyl stearate, cetyl stearate, behenyl behenate, dioctyl maleate, dioctyl sebacate, diisopropyl adipate, cetyl octanoate, diisopropyl dilinoleate.

(5) mono-, di- and tri-glycerides of $C_1$-$C_{30}$ carboxylic acids, e.g., caprylic/capric triglyceride, PEG-6 caprylic/capric triglyceride, PEG-8 caprylic/capric triglyceride.

(6) alkylene glycol esters of C1-C30 carboxylic acids, e.g., ethylene glycol mono- and di-esters, and propylene glycol mono- and di-esters of C1-C30 carboxylic acids e.g., ethylene glycol distearate.

(7) propoxylated and ethoxylated derivatives of the foregoing materials.

(8) $C_1$-$C_{30}$ mono- and poly-esters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated) the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoleate, sucrose hexaoleate, sucrose heptatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7-8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in U.S. Pat. Nos. 2,831,854; 4,005,196; 4,005,195; 5,306,516; 5,306,515; 5,305,514; 4,797,300; 3,963,699; 4,518,772; and 4,517,360.

(9) Vegetable oils and hydrogenated vegetable oils. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

(10) Animal fats and oils (e.g., lanolin and derivatives thereof, cod liver oil).

(11) Fluorine-containing hydrocarbon fluids.

Examples include but are not limited to, hydrofluoroethers from 3M Corporation, and perfluoropolyethers (Fomblin series manufactured by Montefluos, Demnum series manufactured by Daikin Industries and Krytox series manufactured by DuPont Corporation).

(12) Also useful are $C_4$-$C_{20}$ alkyl ethers of polypropylene glycols, $C_1$-$C_{20}$ carboxylic acid esters of polypropylene glycols, and di-$C_8$-$C_{30}$ alkyl ethers. Nonlimiting examples of these materials include PPG-14 butyl ether, PPG-15 stearyl ether, dioctyl ether, dodecyl octyl ether, and mixtures thereof.

3. Inorganic Non-Polar Materials:

Nonlimiting examples of suitable inorganic non-polar materials include, but are not limited to:

Organopolysiloxane oils. Nonlimiting examples of suitable silicones are disclosed in U.S. Pat. No. 5,069,897. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000-centistokes at 25° C. Such polyalkylsiloxanes can be represented by the general chemical formula $R_3SiO[R_2SiO]xSiR_3$ wherein R is an alkyl group having from about 1 to about 30 carbon atoms (preferably R is methyl: or ethyl, more preferably methyl; also mixed alkyl groups can be used in the same molecule), and x is an integer of from about 0 to about 10,000, chosen to achieve the desired molecular weight which can range to over about 10,000,000. Commercially available polyalkylsiloxanes include the polydimethylsiloxanes, which are also known as dimethicones; examples of which include the Vicasil® series sold by General Electric Company and the Dow Corning® series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from about 2 to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2—O]_n$ wherein R is an alkyl group (preferably R is methyl or ethyl, more preferably methyl) and n is an integer from about 3 to about 8, more preferably n is an integer from about 3 to about 7, and even more preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217° C., which primarily contains a mixture of the cyclomethicone tetramer, pentamer, and hexamer (i.e. n=4, 5, and 6).

Dimethiconols are also suitable for use in the composition. These compounds can be represented by the chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. A particularly preferred polyalkylaryl siloxane for use in the present invention is a trimethylpentaphenyl trisiloxane.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

Optional Ingredients

A. Colorants

The cosmetic system may further comprise a colorant. Suitable colorants include, but are not limited to, D&C Yellow No. 7, D&C Red No. 36, FD&C Red No. 4, D&C Orange No. 4, D&C Red No. 6, D&C Red No. 34, FD&C Yellow No. 6, D&C Red No. 33, FD&C Yellow No. 5, D&C Brown No. 1, D&C Red No. 17, FD&C Green No. 3, D&C Blue No. 4, D&C Yellow No. 8, D&C Orange No. 5, D&C Red No. 22, D&C Red No. 21, D&C Red No. 28, D&C Orange No. 11, D&C Yellow No. 10, D&C Violet No. 2, Ext. D&C Violet No. 2, D&C Green No. 6, D&C Green No. 5, D&C Red No. 30, D&C Green No. 8, D&C Red No. 7, FD&C Blue No. 1, D&C Yellow No. 7, D&C Red No. 27, D&C Orange No. 10, D&C Red No. 31, FD&C Red No. 40, D&C Yellow No. 11, Annatto extract, .beta. carotene, guanine, carmine, aluminum powder, ultramarines, bismuth oxychloride, chromium oxide green, chromium hydroxide green, iron oxides, ferric ferrocyanide, manganese violet, titanium dioxide, titanated mica (i.e., mica coated with titanium dioxide), iron oxide titanated mica, zinc oxide, caramel coloring, mica, ferric ammonium ferrocyanide, dihydroxyacetone, guaiazulene, pyrophyllite, bronze powder, copper powder, aluminum stearate, calcium stearate, lactofavin, magnesium stearate, zinc stearate, capsanthin/capsorubin, bentonite, barium sulfate, calcium carbonate, calcium sulfate, carbon black, magnesium carbonate, magnesium silicate, colored silica, silica (including spherical silica, hydrated silica and silica beads), CI 10020, CI 11680, CI 15630, CI 15865, CI 16185, CI 16255, CI 16255; CI 45430, CI 69825, CI 73000, CI-73015, CI-74160, CI-75100, CI-77002, CI-77346, CI-77480, nylon powder, polyethylene powder, ethylene acrylates copolymer powder, methacrylate powder, polystyrene powder, silk powder, crystalline cellulose, starch, bismuth oxychloride, guanine, kaolin, chalk, diatomaceous earth, microsponges, boron nitride and the like. Additionally, lakes or composites of these colorants may also be used. Additional colorants, pigments, and powders useful herein are described in U.S. Pat. No. 5,505,937.

B. Film Forming Agent

The cosmetic system may further comprise a film-forming agent. Preferably, the compositions comprise from greater than 0% to 20%, more preferably, from 0.05% to 10%, and even more preferably from 0.1% to 5%, by weight of the composition, of the film-forming agent.

Examples of suitable film forming agents useful in the compositions of the present kit include:

a) sulfopolyester resins, such as AQ sulfopolyester resins, such as AQ29D, AQ35S, AQ38D, AQ38S, AQ48S, and AQ55S (available from Eastman Chemicals);

b) polyvinylacetate/polyvinyl alcohol polymers, such as Vinex resins available from Air Products, including Vinex 2034, Vinex 2144, and Vinex 2019;

c) acrylic resins, including water dispersible acrylic resins available from National Starch under the trade name "Dermacryl", including Dermacryl LT;

d) polyvinylpyrrolidones (PVP), including Luviskol K17, K30 and K90 (available from BASF), water soluble copolymers of PVP, including PVP/VA S-630 and W-735 and PVP/dimethylaminoethylmethacrylate Copolymers such as Copolymer 845 and Copolymer 937 available from ISP, as well as other PVP polymers disclosed by E. S. Barabas in the Encyclopedia of Polymer Science and Engineering, 2 Ed., Vol. 17, pp. 198-257;

e) high molecular weight silicones such as dimethicone and organic-substituted dimethicones, especially those with viscosities of greater than about 50,000 mPas;

f) high molecular weight hydrocarbon polymers with viscosities of greater than about 50,000 mPas;

g) silicone-acrylate copolymers, including VS-70 (3M), SA-70 (3M), KP-545 (Shin-Etsu)

h) organosiloxanes, including organosiloxane resins, fluid diorganopolysiloxane polymers and silicone ester waxes;

i) polyurethanes, including Polyderm series of polymers from Alzo, Corp.; and j) hydrophobic acrylate copolymers, including the acrylate/alkylmethacrylate copolymer Lipacryl (Rohm & Haas) or its emulsified, water dispersible version Allianz OPT (ISP).

Examples of these polymers and cosmetic compositions containing them are found in PCT publication Nos. WO96/33689, WO97/17058; and U.S. Pat. No. 5,505,937. Additional film forming polymers suitable for use herein include the water-insoluble polymer materials in aqueous emulsion and water soluble film forming polymers described in PCT publication No. WO98/18431. Examples of high molecular weight hydrocarbon polymers with viscosities of greater than about 50,000 mPas include polybutene, polybutene terephthalate, polydecene, polycyclopentadiene, and similar linear and branched high molecular weight hydrocarbons.

Suitable film forming polymers also include organosiloxane resins comprising combinations of $R_3SiO_{1/2}$ "M" units, $R_2SiO$ "D" units, $RSiO_{3/2}$ "T" units, $SiO_2$ "Q" units in ratios to each other that satisfy the relationship $R_nSiO_{(4-n)/2}$ where n is a value between 1.0 and 1.50 and R is a methyl group. Note that a small amount, up to 5%, of silanol or alkoxy functionality may also be present in the resin structure as a result of processing. The organosiloxane resins must be solid at about 25° C. and have a molecular weight range of from about 1,000 to about 10,000 grams/mole. The resin is soluble in organic solvents such as toluene, xylene, isoparaffins, and cyclosiloxanes or the volatile carrier, indicating that the resin is not sufficiently crosslinked such that the resin is insoluble in the volatile carrier. Particularly preferred are resins comprising repeating monofunctional or $R_3SiO_{1/2}$ "M" units and the quadrafunctional or $SiO_2$ "Q" units, otherwise known as "MQ" resins as disclosed in U.S. Pat. No. 5,330,747. In the present invention the ratio of the "M" to "Q" functional units is preferably about 0.7 and the value of n is 1.2. Organosiloxane resins such as these are commercially available such as Wacker 803 and 804 available from Wacker Silicones Corporation, and G.E. 1170-002 from the General Electric Company.

Other suitable silicone film formers may include polyalkylsilsesquioxanes such as, for example, polymethylsilsesquioxane (Resin MK from Wacker) and polypropylsilsesquioxane (DC670 from Dow Corning).

Other materials for enhancing wear or transfer resistance include trimethylated silica. Suitable silicas of this type and cosmetic compositions containing them are described in U.S. Pat. No. 5,800,816.

C. Absorbents

The compositions of the present invention may comprise one or more absorbent materials. These absorbents are useful for achieving the uptake of various fluids that are commonly present on the skin, e.g., perspiration, oil, and/or sebum. Suitable absorbents include, but are not limited to, silicas, silicates, polyacrylates, cross-linked silicones, cross-linked hydrocarbons, activated carbon, starch-based materials (for example cornstarch (topical starch), talc, rice starch, oat starch, tapioca starch, potato starch, legume starches, soy starch, turnip starch), microcrystalline cellulose (for example Avicel®), aluminum starch octenyl succinate (sold by National Starch & Chemical Co. as Dry Flo® Pure, Dry Flo® XT, Dry Flo® PC, and/or Dry Flo® AF (aluminum free grade)), kaolin, calcium silicate, amorphous silicas, calcium carbonate, magnesium carbonate, or zinc carbonate, and mixtures thereof. Some specific examples of the silicates and carbonates useful in the present invention are more fully explained in Van Nostrand Reinhold's Encyclopedia of Chemistry. 4th Ed. pages 155, 169, 556, and 849, (1984).

D. Anti-Acne Actives

Examples of useful anti-acne actives of the present: invention include, but are not limited to, the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

E. Antiperspirant Actives

Antiperspirant actives may also be, included in the compositions of the present invention. Suitable antiperspirant actives include astringent metallic salts, especially the inorganic and organic, salts of aluminum zirconium and zinc, as well as mixtures thereof. Particularly preferred are the aluminum containing and/or zirconium-containing materials, or salts, such as aluminum halides, aluminum chlorohydrate, aluminum hydroxyhalides, zirconyl oxyhalides, zirconyl hydroxyhalides, and mixtures thereof.

F. Anti-Wrinkle and Anti-Skin Atrophy Actives

Examples of anti-wrinkle and anti-skin atrophy actives useful in the present invention include, but are not limited to, retinoic acid and its derivatives (e.g., cis and trans); retinol; retinyl esters; niacinamide, and derivatives thereof; sulfur-containing D and L amino acids and their derivatives and salts, particularly the N-acetyl derivatives, a preferred example of which is N-acetyl-L-cysteine; thiols (e.g., ethane thiol); terpene alcohols (e.g., farnesol); hydroxy acids, phytic acid, lipoic acid; lysophosphatidic acid, alpha-hydroxy acids (e.g., lactic acid and glycolic acid), beta-hydroxy acids (e.g., salicylic acid), and skin peel agents (e.g., phenol and the like).

G. Artificial Tanning Actives and Accelerators

Examples of artificial tanning actives and accelerators useful in the compositions of the present invention include, but are not limited to, dihydroxyacetaone, tyrosine, tyrosine esters such as ethyl tyrosinate, phospho-DOPA, and mixtures thereof.

H. Astringents

The compositions of the present invention may include astringents. Astringents are useful for shrinking pores of the skin. Suitable astringents include, but are not limited to, clove oil, fomes officinalis extract., spiraea ulmaria extract, menthol, camphor, eucalyptus oil, eugenol, menthyl lactate, witch hazel distillate, aluminum salts, tannins, ethanol, and combinations thereof.

I. Hydrophilic Conditioning Agents

The present invention can also comprise or more hydrophilic conditioning agents. Nonlimiting examples of hydrophilic conditioning agents include those selected from the group consisting of polyhydric alcohols, polypropylene glycols, polyethylene glycols, ureas, pyrolidone carboxylic acids, ethoxylated and/or propoxylated $C_3$-$C_6$ diols and triols, alpha-hydroxy $C_2$-$C_6$ carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful hydrophilic conditioning agents include materials such as urea; guanidine; glycolic acid and glycolate salts (e.g., ammonium and quaternary alkyl ammonium); lactic acid and lactate salts (e.g., ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; cationic skin conditioning polymers (e.g., quaternary ammonium polymers such as Polyquaternium polymers); and mixtures thereof. Glycerol, in particular, is a preferred hydrophilic conditioning agent in the present invention. Also useful are materials such as aloe vera in a variety of forms (e.g., aloe vera gel), chitosan and chitosan derivatives (e.g., chitosan lactate, lactamide monoethanolamine); acetamide monoethanolamine; and mixtures thereof. Also useful are propoxylated glycerols as described in propoxylated glycerols described in U.S. Pat. No. 4,976,953.

J. Hydrophobic Conditioning Agents

The composition may comprise one or more hydrophobic conditioning agents. Preferred hydrophobic conditioning agents are selected from the group consisting of mineral oil, petrolatum, lecithin, hydrogenated lecithin, lanolin, lanolin derivatives, $C_7$-$C_{40}$ branched chain hydrocarbons, $C_1$-$C_{30}$ alcohol esters of $C_1$-$C_{30}$ carboxylic acids, $C_1$-$C_{30}$ alcohol esters of $C_2$-$C_{30}$ dicarboxylic acids, monoglycerides of $C_1$-$C_{30}$ carboxylic acids, diglycerides of $C_1$-$C_{30}$ carboxylic acids, triglycerides of $C_1$-$C_{30}$ carboxylic acids, ethylene glycol monoesters of $C_1$-$C_{30}$ carboxylic acids, ethylene glycol diesters of $C_1$-$C_{30}$ carboxylic acids, propylene glycol monoesters of $C_1$-$C_{30}$ carboxylic acids, propylene glycol diesters of $C_1$-$C_{30}$ carboxylic acids, $C_1$-$C_{30}$ carboxylic acid monoesters and polyesters of sugars, polydialkylsiloxanes, polydiarylsiloxanes, polyalkylarylsiloxanes, cyclomethicones having 3 to 9 silicone atoms, vegetable oils, hydrogenated vegetable oils, polypropylene glycol $C_4$-$C_{20}$ alkyl ethers, di $C_8$-$C_{30}$ alkyl ethers, and combinations thereof.

K. Light Diffusers

The compositions may comprise a light diffuser. Light diffusers are useful for improving skin appearance by minimizing the appearance of texture such as pores and fine lines. Suitable light diffusers for inclusion into the compositions of the present system include, but are not limited to silica, nylon, polyethylene, polymethyl methacrylate, polystyrene, methylsiloxane copolymer, polytetrafluoroethylene copolymer, boron nitride, silicone resin powders, silicone rubber powders, ethylene acrylate copolymers, mica, titanium dioxide, iron oxides, zinc oxide, and combinations thereof.

L. Oil-Soluble Polymeric Gelling Agents

The compositions of the present invention may optionally comprise one or more polymeric materials that are oil-soluble and form a gel with hydrophobic materials (e.g., oils) that are contained in the compositions. Such polymers are beneficial for structuring these materials resulting in flexible gels with improved stability and shear-resistance.

Particularly suitable are at least partially cross-linked oil-soluble polymeric materials with a softening point <160° C. Suitable materials come from the chemical groups of PE (polyethylenes), PVA (polyvinyl alcohols) and derivatives, PVP (polyvinylpyrrolidones) and derivatives, PVP/Alkene copolymers, PVP/VA copolymers, PVM/MA (methyl vinyl ether/maleic anhydride) copolymers and their esters and ethers, particularly poly (alkyl vinyl ether-co-maleic anhydride) copolymers, ethylene/VA copolymers, acrylates/alkyl methacrylate copolymer, styrene/isoprene, styrene/ethylene/butylene, styrene/ethylene/propylene, styrene/ethylene/butylene/styrene, styrene/butadiene copolymers, benotnite clays, hectorite clays, organix waxes and silicone waxes. Suitable materials are available e.g. from, Dupont (ELVAX® types), BASF (LUVISKOL® types), Shell (KRATON® polymers), ISP (PVP, GUNTREZ®, GANEX® and ALLIANZ OPT® types) and Rohm & Haas (LIPACRYL®).

M. Hydrophilic Gelling Agent

The compositions of the invention may optionally contain a hydrophilic gelling agent. The gelling agent preferably has a viscosity (1% aqueous solution, 20° C., Brookfield RVT) of at least about 4000 mPas, more preferably at least about 10,000 mPas and even more preferably at least 50,000 mPas.

Suitable hydrophilic gelling agents can generally be described as water-soluble or colloidally water-soluble polymers, and include cellulose ethers (e.g. hydroxyethyl cellulose, methyl cellulose, hydroxypropylmethyl cellulose), bentonite clays, hectorite clays, polyvinylpyrrolidone, polyvinylalcohol, polyquaternium-10, guar gum, hydroxypropyl guar gum, and xanthan gum.

Among suitable hydrophilic gelling agents are acrylic acid/ethyl acrylate copolymers and the carboxyvinyl polymers sold by the B. F. Goodrich Company under the trademark of Carbopol resins. These resins consist essentially of a colloidally water-soluble polyalkenyl polyether crosslinked polymer of acrylic acid crosslinked with from about 0.75% to about 2.00% of a crosslinking agent such as for example polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are hydrophobically-modified cross-linked polymers of acrylic acid having amphipathic properties available under the Trade Name Carbopol 1382, Carbopol 1342 and Pemulen TR-1 (CTFA Designation: Acrylates/10-30 Alkyl Acrylate. Crosspolymer). A combination of the polyalkenyl polyether cross-linked acrylic acid polymer and the hydrophobically modified cross-linked acrylic acid polymer is also suitable for use herein. Other suitable gelling agents suitable for use herein are oleogels such as trihydroxystearin and aluminium magnesium hydroxy stearate. The gelling agents herein are particularly valuable for providing excellent stability characteristics over both normal and elevated temperatures.

Neutralizing agents suitable for use in neutralizing acidic group containing hydrophilic gelling agents herein include sodium hydroxide, potassium hydroxide, ammonium hydroxide, monoethanolamine, diethanolamine and triethanolamine.

N. Crosslinked Silicone Polymers

The composition of the present invention may optionally include a polymer that is non-linear in nature. Suitable polymers for inclusion in the claimed compositions include, but are not limited to polysiloxanes that are crosslinked organopolysiloxane polymer gel networks. For instance, particularly well-suited crosslinked organopolysiloxane polymer gel networks are formed from polymerization of an epoxy functional organosiloxane in the presence of an acid catalyst. The organopolysiloxane polymer a crosslinked organopolysiloxane polymer gel network selected from non-emulsifying polymer gel networks, emulsifying polymer gel networks, and combinations thereof. Specific examples of such are described in U.S. Pat. No. 6,531,540 B1, U.S. Pat. No. 6,538,061 B2, U.S. Pat. No. 6,444,745 B1, U.S. Pat. No. 6,346,583 B1, U.S. Pat. Nos. 5,654,362, 5,811,487, 5,880,210, 5,889,108, 5,929,164, 5,948,855, 5,969,035, 5,977,280, 6,080,394, 6,168,782, 6,177,071, 6,200,581, 6,207,717, 6,221,927, 6,221,979, 6,238,657, and 4,987,169.

Suitable organopolysiloxane polymer network powders include vinyl dimethicone/methicone silsesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200, and hybrid silicone powders that contain a phenyl group such as Shin-Etsu's KSP-300; and Dow Corning's DC 9506.

Preferred organopolysiloxane compositions are dimethicone/vinyl dimethicone crosspolymers. Such dimethicone/vinyl dimethicone crosspolymers are supplied by a variety of suppliers including Dow Corning (DC 9040 and DC 9041), General Electric (Velvesil 125), General Electric (SFE 839), Shin Etsu (KSG-15, 16, 18 [dimethicone/phenyl vinyl dimethicone crosspolymer] and KSG-21 [dimethicone copolyol crosspolymerl), Grant Industries (Gransil™ line of materials), lauryl dimethicone/vinyl dimethicone crosspolymers supplied by Shin Etsu (e.g., KSG-41, KSG-42, KSG-43, and KSG-44), lauryl dimethicone/dimethicone copolyol crosspolymers also supplied by Shin-Etsu (e.g., KSG-31, KSG-32, KSG-33, and KSG-34), and Wacker (Belsil RG-100) Additional polymers from Shin-Etsu which are suitable for use in the present invention include KSG-210, -310, -320, -330, and -340. Crosslinked organopolysiloxane polymer gel networks useful in the present invention and processes for making them are further described in U.S. Pat. Nos. 4,970,252; 5,760,116; 5,654,362; and Japanese Patent Application JP 61-18708.

O. Sunscreen Actives

The cosmetic compositions of this invention may also contain sunscreens, which are chemical absorbers that actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

Classifying the chemical absorbers generally as UV-A or UV-B absorbers is accepted within the industry. However, a more precise classification is one based upon the chemical properties of the sunscreens. There are eight major classifications of sunscreen chemical properties, and that are discussed at length in "*Sunscreens—Development, Evaluation and Regulatory Aspects*," by N. Shaath et al., 2nd. Edition, pages 269-273, Marcel Dekker, Inc. (1997).

The sunscreens useful in the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes (such as avobenzone also known as Parsol®1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP 863,145, EP 517,104, EP 570,838, EP 796,851, EP 775,698, EP 878,469, EP 933,376, EP 893,119, EP 669,323, GB 2,303,549, DE 1,972,184 and WO 93/04665, the entire contents of which are hereby incorporated by reference. Also exemplary of the sunscreens which may be formulated into the compositions of this invention are physical-blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

A wide variety of sunscreens is described in U.S. Pat. Nos. 5,087,445; 5,073,372; and Chapter VIII of *Cosmetics and*

*Science and Technology* (1957) by Segarin et al., pages 189 et seq, the entire contents of each of which are hereby incorporated by reference.

Examples of suitable sunscreens include, but are not limited to: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomethyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N,N-trimethyl-4-(2-oxoborn-3-ylidene methyl)anillinium methyl sulfate, and mixtures thereof.

Sunscreens active in the UV-A and/or UV-B range can also include, but are not limited to:
p-aminobenzoic acid,
oxyethylene (25 mol) p-aminobenzoate,
2-ethylhexyl p-dimethylaminobenzoate,
ethyl N-oxypropylene p-aminobenzoate,
glycerol p-aminobenzoate,
4-isopropylbenzyl salicylate,
2-ethylhexyl 4-methoxycinnamate,
methyl diisopropylcinnamate,
isoamyl 4-methoxycinnamate,
diethanolamine 4-methoxycinnamate,
3-(4'-trimethylammonium)-benzyliden-bornan-2-one methylsulfate,
2-hydroxy-4-methoxybenzophenone,
2-hydroxy-4-methoxybenzophenone-5-sulfonate,
2,4-dihydroxybenzophenone,
2,2',4,4'-tetrahydroxybenzophenone,
2,2'-dihydroxy-4,4'dimethoxybenzophenone,
2-hydroxy-4-n-octoxybenzophenone,
2-hydroxy-4-methoxy-4'-methoxybenzophenone,
-(2-oxoborn-3-ylidene)-tolyl-4-sulfonic acid and soluble salts thereof,
3-(4'-sulfo)benzyliden-bornan-2-one and soluble salts thereof,
3-(4'methylbenzylidene)-d,l-camphor,
3-benzylidene-d,l-camphor,
benzene 1,4-di(3-methylidene-10-camphosulfonic) acid and salts thereof (the product Mexoryl SX described in U.S. Pat. No. 4,585,597,
urocanic acid,
2,4,6-tris[p-(2'-ethylhexyl-1'-oxycarbonyl)-anilino]-1,3,5-triazine,
2-[(p-(tertiobutylamido)anilino]-4,6-bis-[(p-(2'-ethylhexyl-1'-oxycarbonyl)anilino)-1,3,5-triazine,
2,4-bis{[4-(2-ethyl-hexyloxy)]-2-hydroxy)]-phenyl}-6-(4-methoxy-phenyl)-1,3,5-triazine ("TINOSORB S" marketed by Ciba),
the polymer of N-(2 et 4)-[(2-oxoborn-3-yliden)methyl]benzyl]-acrylamide,
1,4-bisbenzimidazolyl-phenylen-3,3',5,5'-tetrasulfonic acid and salts thereof,
the benzalmalonate-substituted polyorganosiloxanes,
the benzotriazole-substituted polyorganosiloxanes (Drometrizole Trisiloxane),
dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that were marketed under the trademark TINOSORB M by Ciba Specialty Chemicals Corp. (Tarrytown, N.Y.), and solubilized 2,2'-methylene-bis-[6-(2H-benzotriazol-2-yl)-4-(methyl)phenol] such as that marketed under the trademark MIXXIM BB/200 by Fairmount Chemical.

Typically combinations of one of more of these sunscreens are used.

The dibenzoyl methane derivatives other than avobenzone are described, for example, in FR 2,326,405, FR and EP 114,607.

Other dibenzoyl methane sunscreens other than avobenzone include (whether singly or in any combination):
2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,41-diisopropyldibenzoylmethane
4,4'-dimethoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane Additional sunscreens that can be used are described in pages 2954-2955 of the *International Cosmetic Ingredient Dictionary and Handbook* (9th ed. 2002). Exact amounts of sunscreens that can be employed will vary depending upon the sunscreen chosen and the desired Sun Protection Factor (SPF) to be achieved. SPF is a commonly used measure of photoprotection of a sunscreen against erythema.

P. Additional Optional Ingredients

The compositions of the present invention may also include ingredients classified as desquamating agents, skin lightening agents, skin soothing and skin healing actives, vitamin compounds and precursors, chelators, enzymes, flavinoids (broadly disclosed in U.S. Pat. Nos. 5,686,082 and 5,686,367), and sterol compounds.

Q. Emulsifiers and Amphiphilic Molecules

The cosmetic system of the present invention may also comprise an emulsifier, an amphiphilic molecule, or mixtures thereof. In a preferred embodiment, the composition contains from 0.05% to 10%, more preferably from 0.1% to 7.5%, and even more preferably from 0.5% to 5%, based on the weight of each individual composition, of an emulsifier or amphiphilic molecule.

Suitable emulsifiers can include any of a wide variety of nonionic, cationic, anionic, and zwitterionic emulsifiers disclosed in the prior patents and other references. See McCutcheon's, Detergents and Emulsifiers, North American Edition (1986), published by Allured Publishing Corporation; U.S. Pat. Nos. 5,011,681; 4,421,769; and 3,755,560.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates., fatty acid amides, acyl lactylates, soaps, and mixtures thereof. Nonlimiting examples of suitable non-silicone-containing emulsifiers for use herein include: polyethylene glycol. 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene-4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

Suitable emulsifiers may also include silicone emulsifiers, which are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain $C_2$-$C_{30}$ pendant side chains. Still other useful dimethicone copolyols include materials having various cationic, anionic, amphoteric, and zwitterionic pendant moieties.

The dimethicone copolyol emulsifiers useful herein can be described by the following general structure:

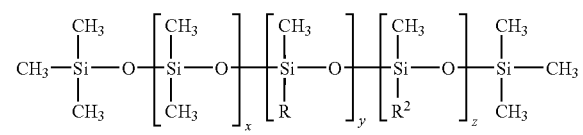

wherein R is $C_1$-$C_{30}$ straight, branched, or cyclic alkyl and $R^2$ is selected from the group consisting of:

$$-(CH_2)_n-O-(CH_2CHR^3O)_m-H,$$

and $$-(CH_2)_n-O-(CH_2CHR^3O)_m-(CH_2CHR^4O)_o-H,$$

wherein n is an integer of from about 3 to about 10; $R^3$ and $R^4$ are selected from the group consisting of H and $C_1$-$C_6$ straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

$$-(CH2)n\text{-}O-R5,$$

wherein R5 is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide sidechains, polydimethylsiloxane polyether copolymers with pendant polypropylene oxide sidechains, polydimethylsiloxane polyether copolymers with pendant mixed polyethylene oxide and polypropylene oxide sidechains, polydimethylsiloxane polyether copolymers with pendant mixed poly(ethylene)(propylene)oxide sidechains, polydimethylsiloxane polyether copolymers with pendant organobetaine sidechains, polydimethylsiloxane polyether copolymers with pendant carboxylate sidechains, polydimethylsiloxane polyether copolymers with pendant quaternary ammonium sidechains; and also further modifications of the preceding copolymers containing pendant $C_2$-$C_{30}$ straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this later material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples include the SILWET series and SILSOFT series available from Crompton/OSi. Other nonlimiting examples of dimethicone copolyols also include lauryl dimethicone copolyol, dimethicone copolyol acetate, dimethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See International Cosmetic Ingredient Dictionary, Fifth Edition, 1993.

Cosmetic and/or Pharmaceutical Uses

The cosmetic system and process of the present invention may be employed for a variety of cosmetic and/or pharmaceutical uses. Examples thereof include, but are not limited to, color cosmetics such as lipsticks, mascaras, foundations, and the like, as well as anti-aging, UV protection and the like.

Without intending to be bound by theory, it is believed that because of the substantial immiscibility of the continuous phases of each individual composition, said substantial immiscibility being facilitated by the difference in solubility parameters of the major ingredients present in each continuous phase, a cosmetic system capable of imparting multiple aesthetic and feel properties can be employed in a single-step application.

EXAMPLES

The following are non-limiting examples of the cosmetic, system of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight-percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

The ratio at which the compositions will be combined will depend upon the type of keratinous substrate being treated and/or the reason for treating the keratinous substrate. Such a determination will be apparent to those of skill in the art.

Lip Compositions

| SEQ | LIP COMPOSITION A<br>RAW MATERIAL/INCI (Trade Name) | % W/W |
|---|---|---|
| A | Hydrogenated Polycyclopentadiene & Caprylic/Capric Triglyceride (Koboguard 5400 CCT) | 40.15 |
| A | TRIMETHYLPENTAPHENYLTRISILOXANE (and) PHENYL METHYL SILOXANE (DC555) | 47.10 |
| B | Ozokerite (Ozokerite Wax Pastilles SP 1021 P) | 6.80 |
| C | Hydrogenated Polycyclopentadiene & Caprylic/Capric Triglyceride (Koboguard 5400 CCT) | 5.00 |
| C | Red 7 | 0.40 |
| D | Colorona Sienna | 0.40 |
| D | Duochrome RG | 0.15 |
|  |  | 100.00 |

Process

1) Disperse pigment Red 7 into hydrogenated Polycyclopentadiene/Caprylic/Capric Triglyceride (Koboguard 5400 CCT)
2) Mix Well Grind it with Triple Roller Mill (Pass 3 times) Check for the dispersion
3) In a separate beaker, weight out SEQ A (Koboguard 5400 CCT and DC 555), mix well till clear under propellor mixing
4) Add Seq B (ozokerite) heat it up to 90 C, till melt and clear
5) Add Pigment Grind (Seq C) mix under moderate propellor mixing
6) Add Pearl Seq D
7) Cool to 25 C under moderating mixing

| SEQ | LIP COMPOSITION B<br>RAW MATERIAL/INCI | % W/W |
|---|---|---|
| A | Hydrogenated Polyisobutene (Polysynlane SV) | 45.15 |
| A | Polybutene (Indopol H100) | 47.10 |
| A | C12-15 ALKYL BENZOATE (Tegosoft TN) | 6.80 |
| A | Polybutene (Higher MW) (Permethyl 104A) | 0.40 |
| A | Hydrogenated Polydecene (Puresyn 150) | 0.40 |
| A | BHT | 0.15 |
|  |  | 100.00 |

Process

1) Add-all the ingredients, and heat it up to 55 C, mix till clear.

The two lip compositions A and B were dispensed at an equal volume and mixed in the palm of the hand just prior to application to the lips. The resulting composition exhibited superior shine.

Foundation Composition

Silicone in Water Composition

| Phase | Trade Name | INCI Name | % w/w |
|---|---|---|---|
| A | Water | Water | 40.90 |
|  | Glycerin | Glycerin | 5.00 |
|  | Hostacerin AMPS | Ammonium Polyacryloyldimethyl Taurate | 0.30 |
|  | Sepigel | Polyacrylamide (and) C13-14 Isoparaffin (and) Laureth-7 | 1.00 |
|  | KF-6100 | Polyglyceryl-3 Disiloxane Dimethicone | 2.00 |
| B | Phenonip | Phenonip | 0.80 |
|  | DC 245 Fluid | Cyclopentasiloxane | 20.00 |
|  | DC 9041 | Dimethicone (and) Dimethicone Crosspolymer | 30.00 |
|  |  | TOTAL | 100.00 |

Water in Silicone Composition

| Phase | Trade Name | INCI Name | % w/w |
|---|---|---|---|
| A1 | DC 245 Fluid | Cyclopentasiloxane | 19.00 |
|  | DC 2-8179 | Nylon-611/Dimethicone Copolymer | 0.50 |
|  | Propylparaben | Propylparaben | 0.20 |
| A2 | SR-1000 | Trimethylsiloxysilicate | 6.00 |
|  | ISOLAN GI 34 | Polyglyceryl-4 Isostearate | 1.50 |
|  | ABIL EM 90 | Cetyl PEG/PPG-10/1 Dimethicone | 1.00 |
|  | BELSIL DMC 6038 | Bis-PEG-15 Methyl Ether Dimethicone | 0.50 |
|  | KP545 | Cyclopentasiloxane and ACRYLATES/DIMETHICONE COPOLYMER | 4.70 |
|  | ITT-Treated pigments | Pigments | 18.00 |
| A3 | SUNSPHERE H 51 | Silica | 3.00 |
|  | ORGASOL 2002 | Nylon-12 | 1.00 |
| A4 | Bentone 38V | Disteardimonium Hectorite | 1.00 |
|  | Propylene Carbonate | Propylene Carbonate | 0.52 |
| B | Water | Water | 40.28 |
|  | Sodium Chloride | Sodium Chloride | 1.00 |
|  | HYDROLITE-5 | Pentylene Glycol | 0.50 |
|  | Sodium Dehydroacetate Monohydrate | Sodium Dehydroacetate | 0.20 |
|  | Methylparaben | Methylparaben | 0.20 |
|  | BRIJ 30 | Laureth-4 | 0.50 |
|  | Phenoxyethanol | Phenoxyethanol | 0.40 |
|  |  | TOTAL | 100.00 |

The silicone-in-water emulsion and the water-in-silicone emulsion were dispensed at an equal volume and mixed in the palm of the hand just prior to application to the face. The resulting composition exhibited superior hydration and good wear.

What is claimed is:

1. A cosmetic system capable of imparting multiple aesthetic benefits onto skin in a single application comprising a multi-unit receptacle containing:
   a first receptacle containing at least a first lip composition having a continuous phase whose major ingredient comprises an inorganic non-polar material selected from at least one member of the group consisting of polyalkylsiloxanes, cyclic polyalkylsiloxanes, dimethiconols, and polyalkylarylsiloxanes and wherein the first composition also comprises a film-forming agent; and
   a second receptacle containing at least a second lip composition having a continuous phase whose major ingredient is a straight or branched chain hydrocarbon;
   wherein one of said first and second lip compositions provides the aesthetic benefit of long wear and a second of said first and second lip compositions provides the aesthetic benefit of shine, and wherein the major ingredient of the first lip composition and the major ingredient of the second lip composition are substantially immiscible with each other.

2. The system of claim 1, wherein the major ingredient of the first composition is a polyalkylaryl siloxane.

3. The system of claim 1, wherein the major ingredient of the first composition is a polyalkyl siloxane.

4. The system of claim 3, wherein the polyalkylsiloxane is a cyclic polyalkylsiloxane.

5. The system of claim 1, wherein the major ingredient of the first composition is a trimethylpentaphenyl trisiloxane.

6. The system of claim 1, wherein the hydrocarbon comprises polybutene.

7. The system of claim 1, wherein the hydrocarbon comprises hydrogenated polyisobutene.

8. The cosmetic system of claim 1, wherein the film-forming agent is selected from the group consisting of sulfopolyester resins, polyvinylacetate/polyvinyl alcohol polymers, acrylic resins, polyvinylpyrrolidones, high molecular weight silicones, high molecular weight hydrocarbon polymers having a viscosity greater than about 50,000 mPas, silicone-acrylate copolymers, organosiloxanes, polyurethanes, hydrophobic acrylate copolymers, and organosiloxane resins.

9. The cosmetic system of claim 1, wherein the second composition further comprises hydrogenated polydecene.

10. A cosmetic system capable of imparting multiple aesthetic benefits onto skin in a single application comprising a multi-unit receptacle containing:
a first receptacle containing at least a first composition which is a silicone-in-water emulsion having a continuous phase whose major ingredient is water and wherein the first composition also comprises a hydrophilic or hydrophobic conditioning agent so as to provide a conditioning effect upon application to the skin;
a second receptacle containing at least a second composition which is a water-in-silicone emulsion having a continuous phase whose major ingredient comprises an inorganic non-polar material selected from at least one member of the group consisting of polyalkylsiloxanes, cyclic polyalkylsiloxanes, dimethiconols, and polyalkylarylsiloxanes so as to provide an effect of long wear upon application to the skin.

11. The system of claim 10, wherein the second composition further comprises a crosslinked silicone polymer.

12. The system of claim 10, wherein the second composition further comprises cyclopentasiloxane.

13. The system of claim 10, wherein the second composition further comprises a dimethicone copolymer.

14. The system of claim 10, wherein the second composition further comprises a colorant.

15. A process for treating lips with a cosmetic system capable of imparting multiple aesthetic benefits onto lips in a single application, comprising:
providing a first receptacle containing at least a first lip composition having a continuous phase whose major ingredient comprises an inorganic non-polar material selected from at least one member of the group consisting of polyalkylsiloxanes, cyclic polyalkylsiloxanes, dimethiconols, and polyalkylarylsiloxanes and wherein the first composition also comprises a film-forming agent; and
providing a second receptacle containing at least a second lip composition having a continuous phase whose major ingredient is a straight or branched chain hydrocarbon;
wherein one of said first and second lip compositions provides the aesthetic benefit of long wear and a second of said first and second lip compositions provides the aesthetic benefit of shine, and wherein the major ingredient of the first lip composition and the major ingredient of the second lip composition are substantially immiscible with each other; and
combining the first and second compositions just prior to or during their application onto the lips.

16. The process of claim 15, wherein the major ingredient of the first composition is a polyalkylaryl siloxane.

17. The process of claim 15, wherein the major ingredient of the first composition is a polyalkyl siloxane.

18. The process of claim 17, wherein the polyalkylsiloxane is a cyclic polyalkylsiloxane.

19. The process of claim 15, wherein the major ingredient of the first composition is a trimethylpentaphenyl trisiloxane.

20. The process of claim 15, wherein the hydrocarbon comprises polybutene.

21. The process of claim 15, wherein the hydrocarbon comprises hydrogenated polyisobutene.

22. The process of claim 15, wherein the film-forming agent is selected from the group consisting of sulfopolyester resins, polyvinylacetate/polyvinyl alcohol polymers, acrylic resins, polyvinylpyrrolidones, high molecular weight silicones, high molecular weight hydrocarbon polymers having a viscosity greater than about 50,000 mPas, silicone-acrylate copolymers, organosiloxanes, polyurethanes, hydrophobic acrylate copolymers, and organosiloxane resins.

23. The process of claim 15, wherein the second composition further comprises hydrogenated polydecene.

24. A process for treating skin with a cosmetic system capable of imparting multiple aesthetic benefits onto skin in a single application, comprising:
providing a first receptacle containing at least a first composition which is a silicone-in-water emulsion having a continuous phase whose major ingredient is water and wherein the first composition also comprises a hydrophilic or hydrophobic conditioning agent so as to provide a conditioning effect upon application to the skin;
providing a second receptacle containing at least a second composition which is a water-in-silicone emulsion having a continuous phase whose major ingredient comprises an inorganic non-polar material selected from at least one member of the group consisting of polyalkylsiloxanes, cyclic polyalkylsiloxanes, dimethiconols, and polyalkylarylsiloxanes so as to provide an effect of long wear upon application to the skin; and
combining the first and second compositions just prior to or during their application onto the skin.

25. The process of claim 24, wherein the second composition further comprises a crosslinked silicone polymer.

26. The process of claim 24, wherein the second composition further comprises cyclopentasiloxane.

27. The process of claim 24, wherein the second composition further comprises a dimethicone copolymer.

28. The process of claim 24, wherein the second composition further comprises a colorant.

29. The process of claim 24, wherein the conditioning effect comprises a hydration effect.

30. The system of claim 10, wherein the conditioning effect comprises a hydration effect.

31. The system of claim 1, wherein first composition, the second composition or both the first and second compositions contains a colorant.

* * * * *